United States Patent [19]

November et al.

[11] Patent Number: 4,668,362

[45] Date of Patent: May 26, 1987

[54] METHOD OF ELIMINATING ELECTROPHORETIC RATE DIFFERENTIALS

[76] Inventors: Daniel November, 82-11 Greenfell St., Kew Gardens, Queens, N.Y. 11415; Ting C. Lee, 6-A Ridgewood Ave., Ossining, N.Y. 10562; Alexander Bsales, 87 Rutgers Pl., Clifton, N.J. 07013

[21] Appl. No.: 757,384

[22] Filed: Jul. 22, 1985

Related U.S. Application Data

[63] Continuation-in-part of Ser. No. 574,342, Jan. 27, 1984, abandoned.

[51] Int. Cl.$^4$ ............................................. B01D 57/02
[52] U.S. Cl. ................................................. 204/182.8
[58] Field of Search ......................... 204/182.8, 299 R

[56] References Cited

U.S. PATENT DOCUMENTS

| | | | |
|---|---|---|---|
| 3,677,930 | 7/1972 | Meshbane et al. | 204/180 G |
| 3,856,655 | 12/1974 | Roberts | 204/299 R |
| 3,980,540 | 9/1976 | Hoefer | 204/180 G |
| 4,142,960 | 3/1979 | Hahn et al. | 204/180 G |
| 4,224,134 | 9/1980 | Hoefer et al. | 204/299 R |
| 4,305,799 | 12/1981 | Shwarz et al. | 204/180 G |
| 4,374,723 | 2/1983 | Vesterberg | 204/299 R |

OTHER PUBLICATIONS

Heftmann, E., *Chromatography* 2d Ed., Reinhold Publishing Co., New York, pp. 235-237 (1967).

*Primary Examiner*—Howard S. Williams
*Attorney, Agent, or Firm*—M. K. Silverman

[57] ABSTRACT

The disclosure relates to a method for substantially eliminating electrophoretic rate differentials between simultaneously disposed side-by-side lanes of test samples. The method includes the steps of defining and vertically orienting an elongate, solid rectangular volume of a host material having substantially uniform pore sizes, the material having a thin cross-section, the volume having a vertical axis aligned with the gravity vector, the rectangular volume having first and second vertical bases; embedding several test samples within a corresponding number of wells formed within an upper edge of the rectangular volume of host material; forming an electro-conductive fluid circuit across the vertical length of the volume of host material; applying an electrical potential in the range of 3,000 to 5,000 volts across the fluid circuit, the direction of the electrical potential being substantially in alignment with the gravity vector; providing the volume of host material with a vertical length in the range of 40 to 100 centimeters; and uniformly and rapidly controlling thermal values within the host material as the electrical potential is applied, to maintain the temperature of the host material in the range of 50 to 60 degrees Centigrade.

6 Claims, 5 Drawing Figures

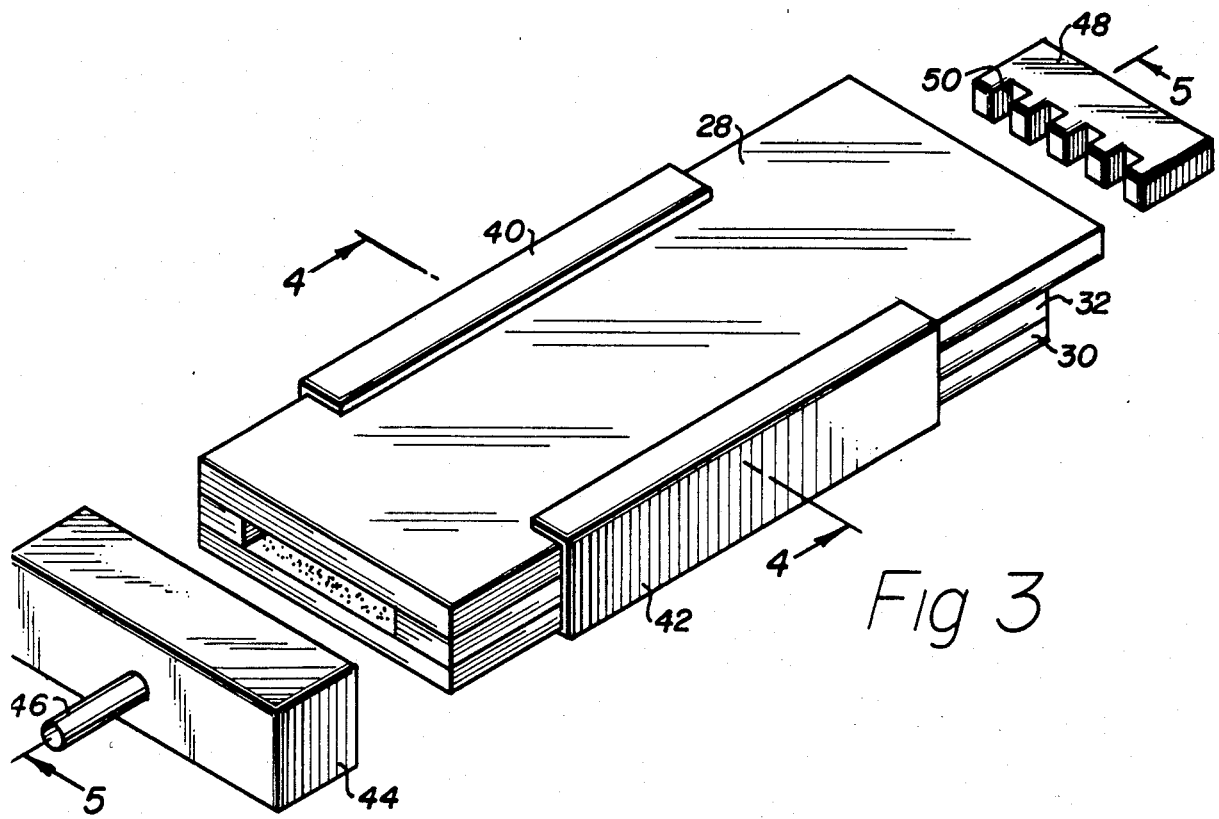
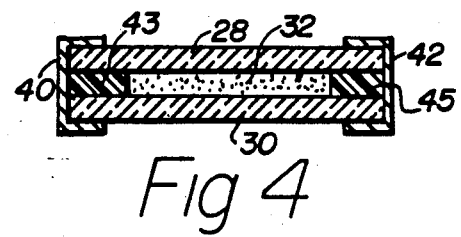
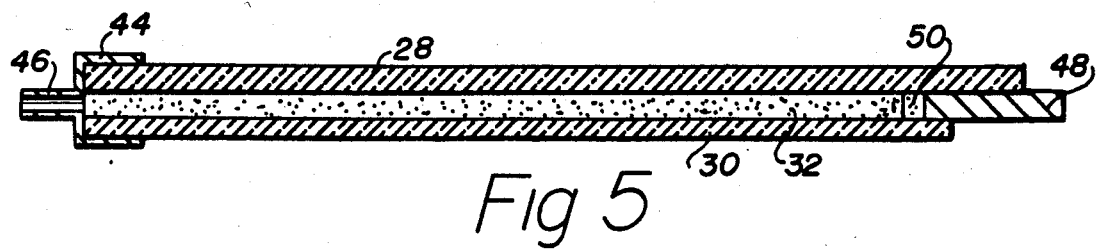

METHOD OF ELIMINATING ELECTROPHORETIC RATE DIFFERENTIALS

REFERENCE TO RELATED APPLICATION

This case is a continuation-in-part of application Ser. No. 574,342, dated Jan. 27, 1984, entitled "Nucleic Fluid Constituent Sequencer", now abandoned.

BACKGROUND OF THE INVENTION

The present invention relates to a method of eliminating electrophoretic rate differentials in the analysis of nucleotides.

In the prior art, it was necessary to subject a DNA fragment (genetic material) to complex chemical and physical testing in order to determine the "spelling" of a genetic "word". Typically, such techniques involved the use of an electron microscope or X-ray difraction in order to, often quite laboriously, determine which of the four basic nucleotides were present at each of many thousands of possible locations.

Recently, the prior art has seen the usage of electrophoresis techniques applied to acrylimite gels embedded with genetic material to bring about separations of the nucleic acids within the DNA molecule. Electrophoresis techniques involve the usage of considerable voltage in order to force a migration of the nucleic acid through the acrylimite gel, this being under the influence of both the voltage and the gravity vector.

A problem in such prior art techniques, one example of which exists in U.S. Pat. No. 4,224,134 to Hoefer, was that the heat generated by the necessary voltage often operated to degrade both the integrity of the test material and to reduce the readability of the test results in that the acrylimite gel is ideally kept at about 53° Centigrade and, thereby, is structurally vulnerable to excursions of heat and temperature.

In addition, the methodology of holding the gel during the period of testing and thereafter has contributed to the problem of structural and chemical integrity of the gel, and therefore the reliability of the test results.

Prior art attempts to deal with the above problem of heat and temperature excursions have related to reducing the voltage used in the electrophoresis process; however, as voltage is reduced, the velocity at which the DNA material will travel through the vertical gel is reduced, thereby considerably increasing the time required for a given study and, in addition, often reducing the number of letters within a DNA sequence that can be accurately measured. Accordingly, the prior art has been aware that a maximum voltage applied to the acrylimite gel is desirable so long as the temperature of the gel can be controlled. However, prior efforts to achieve this result have not been satisfactory. Therefore, it is to this problem that the present invention is addressed.

Other relevant prior art of which the Applicants are aware includes U.S. Pat. Nos. 3,677,930 (1972) to Meshbane; 3,980,540 (1976) to Hoeffer; 4,305,799 (1981) to Schwartz; and 4,142,960 to Hahn. The publication of E. Heftmann, entitled *Chromotography*, 2nd Edition, Reinhold Publishing Co., New York (1967) pp. 235 to 237 sets forth the theory of high voltage electrophoresis.

SUMMARY OF THE INVENTION

The present invention relates to a method for substantially eliminating electrophoretic rate differentials between simultaneously disposed side-by-side lanes of test samples, the method comprising the steps of defining and vertically orienting an elongate, solid rectangular volume of a host material having substantially uniform pore sizes therein; the material having a thin cross-section, said volume having a vertical axis aligned with the gravity vector, said rectangular volume having first and second vertical bases; embedding a plurality of test samples within a corresponding plurality of wells formed within an upper edge of said rectangular volume of host material forming an electro-conductive fluid circuit across the vertical length of said volume of host material applying an electrical potential in the range of 3,000 to 5,000 volts across said fluid circuit, the direction of said electrical potential being substantially in alignment with the gravity vector providing said volume of host material with a vertical length in the range of 40 to 100 centimeters; and uniformly and rapidly controlling thermal values within the host material as said electrical potential is applied thereacross, to maintain the temperature of the host material in the range of 50 to 60 degrees Centigrade, whereby the combined effects of gravity, electrical potential, molecular mobility, and capillary pressure, will cause downwardy directed lanes to flow from each of said well-embedded test samples, in which the fractionation rate differentials between the respective side-by-side lanes will be substantially eliminated by reason of the combined effect of applying said level of electrical potential while uniformly maintaining thermal values in the host material and thereby within each of said test lanes.

It is an object of the present invention to provide an electrophoresis method for the analysis of fractionated nucleic constituents which will provide more efficient heat removal and, thereby, permit operation at voltages higher than heretofore possible.

A further object is to provide a method of the above-referenced type in which test results can be obtained more efficiently and accurately by reason of a more uniform distribution of heat in the test medium and, as necessary, more efficient removal of heat from such medium.

Further objects and advantages of the present invention will become apparent from the hereinafter set forth Detailed Description of the Invention, the Drawings, and the Appended Claims.

BRIEF DESCRIPTION OF THE DRAWINGS

FIG. 3 is an exploded perspective view showing the loading of the gel-like host material into the apparatus, and placement of the test sample into said gel.

FIG. 4 is a cross-sectional view taken along line 4—4 of FIG. 3.

FIG. 5 is a longitudinal, cross-sectional view taken along line 5—5 of FIG. 3.

DETAILED DESCRIPTION OF THE INVENTION

Figure 1:
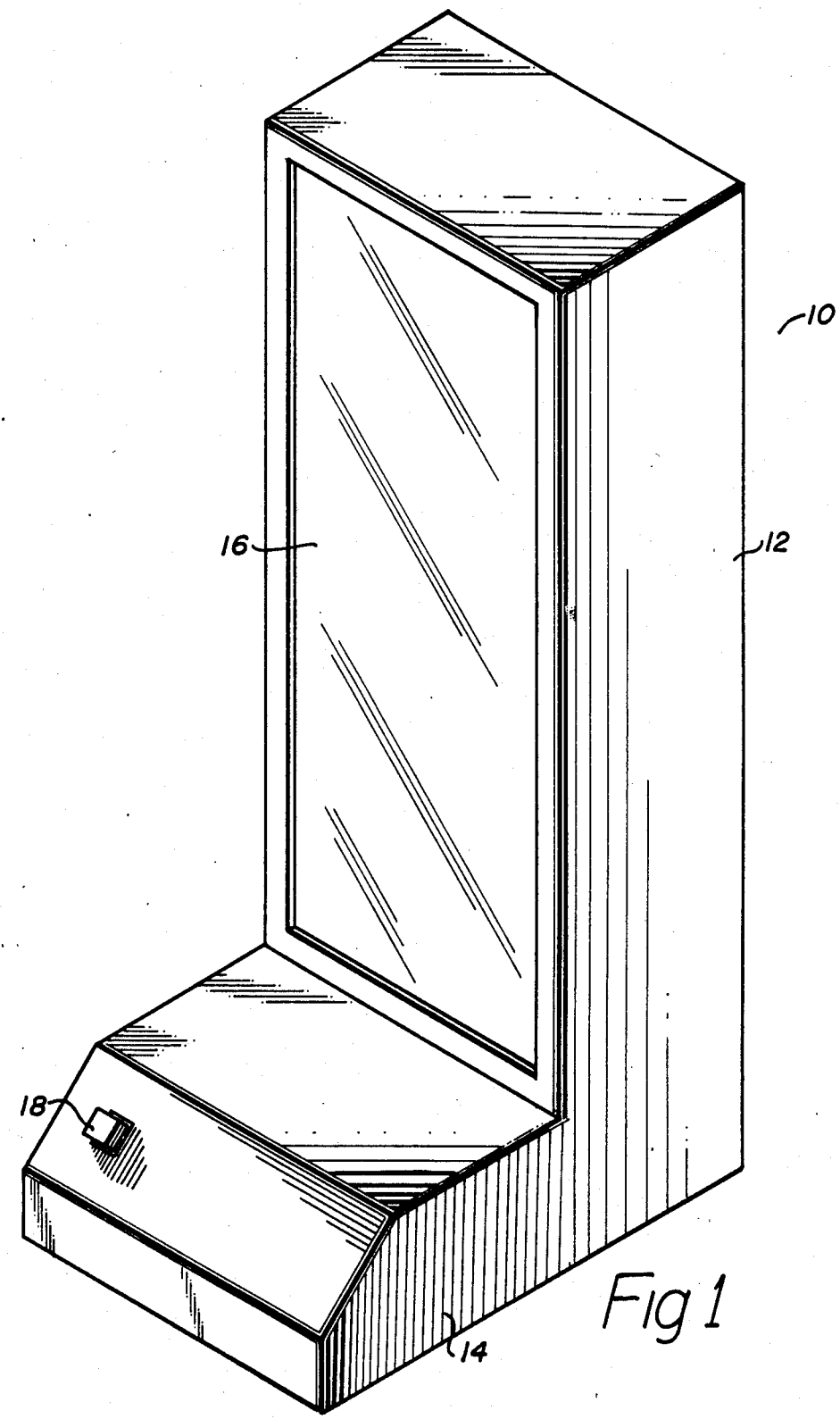
FIG. 1 is a perspective view of the present electrophoresis device.

The present electrophoresis system for nucleic constituent sequencing is shown in external perspective view in FIG. 1. The generalized configuration of the structure involves a vertical aspect 12 and a horizontal aspect 14. Secured in the vertical aspect 12 is a vertical plate 16 formed of a material such as glass. The preferred length of said plate 16 is about one meter and its preferred width is about 0.25 meters. Button 18 is an ambient temperature control actuator.

Figure 2:
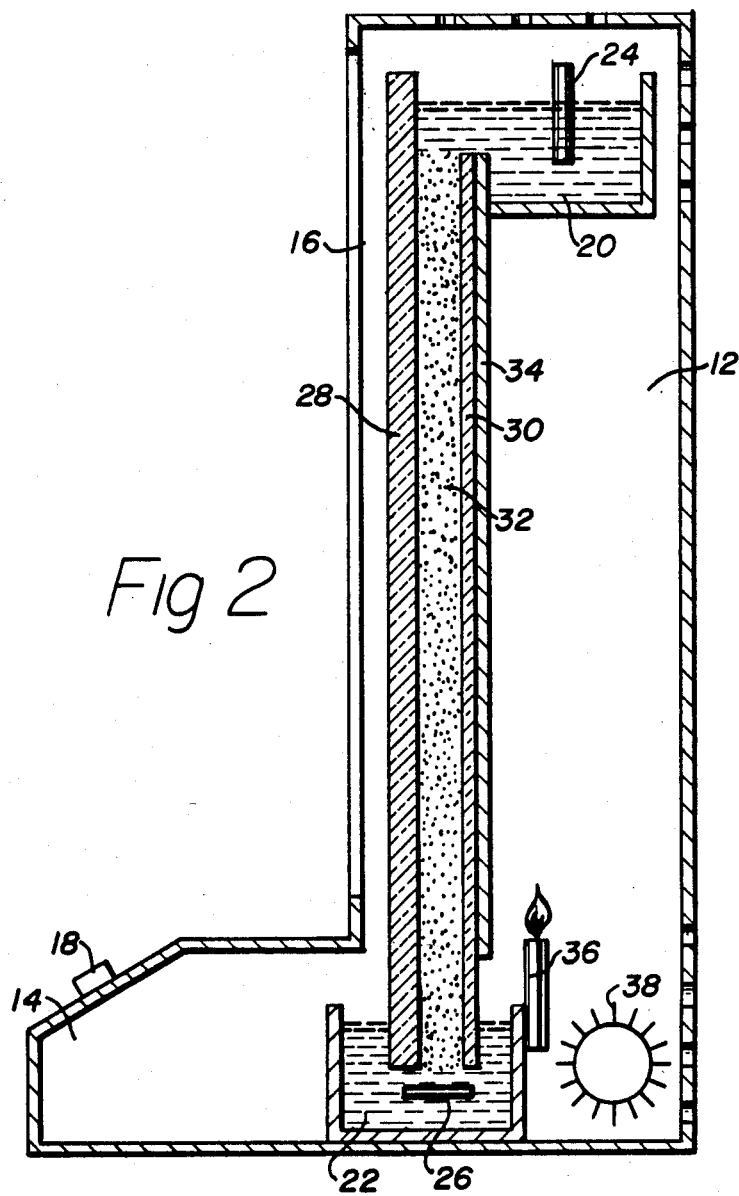
FIG. 2 is a longitudinal, cross-sectional view of the device of FIG. 1.

In FIG. 2 is shown in cross-sectional schematic view the material elements of the present invention. These include a "gel sandwich" comprising a first vertical plate 28, a second vertical plate 30 and a solution-absorbent host material 32, such as acrylimite gel, disposed therebetween. It is noted that the second plate 30 is offset from said first plate 28 and is in contact with the test sample host material, i.e. the gel 32. Through this sandwich-like arrangement, the gel 32 is formed into an elongate solid rectangular mass enclosed upon its major vertical bases by said first and second plates, 28 and 30 respectively.

Also included in the present invention is a longitudinal heat sink 34 which, preferably, is formed of a material such as aluminum. This heat sink is in thermal communication with said second plate 30. It is to be appreciated that heat sink 24 comprises means for the uniform distribution of heat throughout the gel 32. In a preferred embodiment, the gel is maintained at a temperature of 53° Centigrade.

At the top of FIG. 2, there is shown an upper solution chamber 20 filled with a conductive buffering solution. Similarly, at the bottom of FIG. 2, is shown a lower solution chamber 22 filled with a second conductive buffering solution.

In each of said chambers 20 and 22 there are electrodes, 24 and 26 respectively, which comprise means for applying an electrical potential across the vertical length of the gel and between the upper and lower solution chambers. This vertical potential is in the neighborhood of 3000 to 5000 volts with an amperage of about 30 milliamps.

In order to assist in the maintenance of an ambient temperature generally falling between 50° and 60° Centigrade, there is provided means for controlling the temperature of the system in the region of heat sink 34. Said temperature control means includes a heating element 36 and a blower element 38. The blower element may be used with the heating element in order to speed the flow of heat to the gel or, alternatively, the blower may be used without the heating element to assist the heat sink 34 in the cooling of the gel 32.

It is to be appreciated that the gel comprises a solution-absorbent material having a substantially uniform pore size. A host material of this characteristic is capable of absorbing the tagging solution within the chambers, 20 and 22, so that appropriate reactions with the test sample will occur throughout the entire length of the host material or gel 32, as the test sample, through capillary action and electrical potential, works it way through the pore structure of the gel into contact with the buffer solution. In a preferred embodiment, the host material is capable of accommodating at least four vertical streams of test results so that the respective sequence of a family of fractionated nucleic material, such as is necessary in DNA sequencing, can be defined. The separation occurs as a function of the molecular length of the test sample and, thereby, provides an appropriate distribution of molecular lengths of the test sample. By providing each of the necessary reactive solutions for each of the "test streams," it is possible to electrophoretically resolve, according to molecular length, the so-called "genetic alphabet" of genetic information molecules having more than 1000 nucleotides.

In this apparatus, there is no use made of Ph gradients; rather, the separation of fractions takes place based upon the mobility of the individual fragments through the acrylimite gel which, of necessity, must have a uniform pore size in order to assure accuracy of result. The pore size will determine the mobility of a particular sized fragment, i.e. smaller fragments will readily pass through the pores moving further "downstream" while the larger fragments will be retarded by interaction with the pore cross-linking system and will appear further "upstream" within the gel 32.

Through the structure of FIG. 2, it is determined that voltages in the area of 4000 volts may be obtained while maintaining the gel at an acceptably low temperature, e.g. in the range of 50° to 60° Centigrade. The maintenance of such a low temperature is necesary to maintain the integrity of the test results, particularly in multi-stream testing and experiments wherein the different tagging solutions may have error induced thereinto in different degress when the gel becomes overheated. Accordingly, where cross-comparison between different nucleotides at various length sequences is necessary, it is of great importance that skewed errors not be induced into one or more of the test streams.

In the prior art, it has been found that, at temperatures in the neighborhood of 3,000 to 4,000 volts, most of the error will be induced toward the streams that are located in the transverse middle of the gel. In the present device, it has been found that through the use of heat sink 34 for heat removal and, where necessary, operation of the fan 38, the heat sink will assure uniformity in application of heat from the heater 36 to attain the desired uniform level of gel temperature not obtainable in the prior art. In the present design, voltages of 4,000 volts, which make possible much faster reaction as well as the securement of more data, can be employed because of the greater efficiency in heat distribution and, if necessary, heat removal from gel 32 by the fan 38.

With reference to FIG. 3 there is shown an exploded perspective view of the hardware used in the filling of the "plate sandwich"; also shown is implement 48 used in providing the various wells for different test samples. More particulary, there is shown a so-called fill adapter 44 also termed a fill boot which, preferably, is formed of an elastomeric material. The fill boot is, as shown in FIG. 3 and longitudinal view of FIG. 5, a frusto-rectangular adapter suitable for fluid-tight placement over the bottom surface of the gel 32 and about the lower end of the vertical plates 38 and 30. After the fill adapter 44 has been put into place, an entry channel 46 is used for the gel to be pumped therethrough and, therefrom between plates 28 and 30.

It is noted that the plate sandwich itself is secured through the use of clamps 40 and 42 (FIGS. 3 and 4), and spacer elements 43 and 45 (FIG. 4) may be used in order to assure the desired offset between the upper and lower plates 28 and 30 respectively.

In order to embed each of a number of test samples appropriately within the top of the rectangular gel structure, an embedding implement 48 (see FIGS. 3 and 5) is employed. This embedding implement is provided with step-tooth shape which imprints upon the gel a series of wells which are suitable for the placement thereinto of the various fractionated molecules to be tested.

As noted above, it has been found that the use of higher voltages than those previously thought possible have, in conjunction with the above disclosed apparatus, made possible certain fractionated nucleic sequencing testing and investigation not heretofore achievable in the prior art.

After electrophoretic separation has occurred, which typically takes about five hours, the plate sandwich will be separated with the gel adhering to one plate thereof and not to the other. This is accomplished by simple siliconization of one of the plates, thereby acting as an adhesion-repulsion mechanism and assuring that the gel will stick only to the untreated side. However, before this step occurs, all of the "reactive streams" will be photographed with standard X-ray film and developed employing techniques termed autoradiography. That is, the film is exposed to radioactive particles which strike the film and leave their tracks behind. Following appropriate exposure, the film is removed in a light-safe environment and developed as standard X-ray film, yielding a pattern of radio-opague fragments. The fragments themselves literally determine the molecular sequence and can be read in linear fashion. In one notable application (recited above), the linear sequencing can be used to determine the genetic alphabet of certain DNA material.

While there have been shown and described preferred embodiments of the present invention, it will be understood that the invention may be embodied otherwise than as herein specifically illustrated and described; and that within said embodiments certain changes in the detail and construction, and the form and arrangement of the parts, may be made without departing from the underlying idea or principles of this invention within the scope of the appended clams.

Having thus described our invention, what we claim as new, useful and non-obvious is:

1. A method for substantially eliminating electrophoretic rate differentials between simultaneously disposed side-by-side lanes of test samples, said lanes co-aligned vertically with the gravity vector, the method comprising the steps of:
    (a) defining and vertically orienting an elongate, solid rectangular volume of a host material having substantially uniform pore sizes therein, the material having a thin cross-section, said rectangular volume having first and second vertical bases;
    (b) providing said volume of host material with a vertical length in the range of 40 to 100 centimeters;
    (c) embedding a plurality of test samples within a corresponding plurality of wells formed within an upper edge of said rectangular volume of host material;
    (d) forming an electro-conductive fluid circuit across the vertical length of said volume of host material;
    (e) applying an electrical potential in the range of 3,000 to 5,000 volts across said fluid circuit, the direction of said electrical potential being substantially in alignment with the gravity vector; and
    (f) uniformly and rapidly controlling thermal values within the host material as said electrical potential is applied thereacross, to maintain the temperature of the host material in the range of 50 to 60 degrees Centigrade, whereby the combined effects of gravity, electrical potential, molecular mobility, and capillary pressure will cause downwardly directed lanes to flow from each of said well-embedded test samples, in which the fractionation rate differentials between the respective side-by-side lanes will be substantially eliminated by reason of the combined effect of applying said level of electrical potential while uniformly maintaining thermal values in the host material and thereby within each of said test lanes.

2. The method as recited in claim 1 wherein Step (a) defines a length of about one meter, thereby permitting high velocity migration of test samples at said elevated electrical potential.

3. The method as recited in claim 1 in which Step (a) defines a width of about 0.25 meters of said host material.

4. The method as recited in claim 1 in which Step (f) of heat removing comprises the step of:
    placement of a heat sink in thermal communication with at least one vertical base of the host material.

5. The method as recited in claim 4 in which Step (f) includes the step of thermostatically controlling the temperature of the host material using heating and cooling means.

6. The method as recited in claim 4, further comprising the step of:
    (h) maintaining a desired pressure within said host material applied from the vertical bases thereof.

* * * * *